(12) United States Patent
Fanara et al.

(10) Patent No.: US 8,946,229 B2
(45) Date of Patent: Feb. 3, 2015

(54) FORMULATIONS

(75) Inventors: Domenico Fanara, Wanze (BE); Monique Berwaer, Ham-sur-Heure-Nalinnes (BE); Anthony Guichaux, Fribourg (CH); Michel Deleers, Linkebeek (BE)

(73) Assignee: UCB, Inc., Smyrna, GA (US)

( * ) Notice: Subject to any disclaimer, the term of this patent is extended or adjusted under 35 U.S.C. 154(b) by 1429 days.

(21) Appl. No.: 12/230,420

(22) Filed: Aug. 28, 2008

(65) Prior Publication Data

US 2009/0047344 A1    Feb. 19, 2009

Related U.S. Application Data

(62) Division of application No. 10/501,359, filed as application No. PCT/EP03/00260 on Jan. 14, 2003, now abandoned.

(30) Foreign Application Priority Data

Jan. 15, 2002   (EP) .................................... 02000871

(51) Int. Cl.
*A61K 31/495* (2006.01)
*A61K 9/20* (2006.01)
*A61P 27/14* (2006.01)
*A61K 9/00* (2006.01)
*A61K 9/68* (2006.01)
*A61K 9/28* (2006.01)

(52) U.S. Cl.
CPC ............. *A61K 9/0095* (2013.01); *A61K 9/0056* (2013.01); *A61K 9/0058* (2013.01); *A61K 9/2086* (2013.01); *A61K 9/2826* (2013.01); *A61K 31/495* (2013.01)
USPC .......................... 514/255.04; 424/464; 514/58

(58) Field of Classification Search
USPC ................ 424/464; 514/255.04, 58
See application file for complete search history.

(56) References Cited

U.S. PATENT DOCUMENTS

| | | | |
|---|---|---|---|
| 4,238,510 A | 12/1980 | Cherukuri et al. | |
| 4,260,596 A * | 4/1981 | Mackles | 424/440 |
| 5,344,659 A | 9/1994 | Kurihara et al. | |
| 5,380,530 A | 1/1995 | Hill | |
| 5,419,898 A | 5/1995 | Ikejiri et al. | |
| 5,460,825 A * | 10/1995 | Roche et al. | 424/470 |
| 5,543,155 A | 8/1996 | Fekete et al. | |
| 5,866,179 A | 2/1999 | Testa | |
| 5,876,759 A | 3/1999 | Gowan, Jr. | |
| 6,172,095 B1 | 1/2001 | Cupps et al. | |
| 6,245,353 B1 | 6/2001 | Tritthart et al. | |
| 6,319,513 B1 | 11/2001 | Dobrozsi | |
| 6,627,234 B1 | 9/2003 | Johnson et al. | |
| 2003/0035839 A1 * | 2/2003 | Hirsh et al. | 424/471 |
| 2003/0206948 A1 | 11/2003 | Gergely et al. | |
| 2003/0215503 A1 * | 11/2003 | Havlir et al. | 424/465 |
| 2004/0028772 A1 | 2/2004 | Andersen | |
| 2004/0170690 A1 | 9/2004 | Fanara et al. | |

FOREIGN PATENT DOCUMENTS

| | | |
|---|---|---|
| EP | 0 636 364 | 2/1995 |
| EP | 0 811 374 | 12/1997 |
| EP | 0 890 358 | 1/1999 |
| WO | 99/01133 | 1/1999 |
| WO | 99/49843 | 10/1999 |
| WO | 00/35298 | 6/2000 |
| WO | 02/13781 | 2/2002 |

OTHER PUBLICATIONS

International Search Report issued in the International (PCT) Application PCT/EP03/00260, mailed Feb. 19, 2003.
"drug." The American Heritage ® Dictionary of the English Language, Fourth Edition, Houghton Mifflin Company, 2004, Answers. com, Dec. 9, 2006, http://www.answers.com/topic/drug p.1.

* cited by examiner

*Primary Examiner* — Lezah Roberts
(74) *Attorney, Agent, or Firm* — Wenderoth, Lind and Ponack, L.L.P.

(57) ABSTRACT

The present invention relates to pharmaceutical compositions for oral administration of active compounds.

15 Claims, No Drawings

FORMULATIONS

This application is a divisional of Ser. No. 10/501,359, filed Jul. 15, 2004 now abandoned which is a 371 U.S. national stage of International Application No. PCT/EP03/00260 filed Jan. 14, 2003, which are incorporated herein in their entirety.

The present invention relates to pharmaceutical compositions for oral administration of active compounds.

The active compounds contemplated for use in this invention are 2-[4-(diphenylmethyl)-1-piperazinyl]-acetic acids and their amides having the general formula I

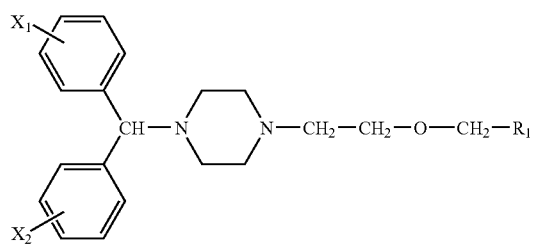

Formula I wherein
$R_1$ is a —COOH group or a —CONH$_2$ group, and
$X_1$ and $X_2$, taken separately, each represent a hydrogen atom, a halogen atom, a straight-chain or branched $C_1$-$C_4$ alkoxy group or a trifluoromethyl group
as well as their pharmaceutically acceptable salts, geometrical isomers, enantiomers, diastereomers and mixtures thereof.

The compounds according to formula I are orally active and selective histamine $H_1$-receptor antagonists. They are described in EP 0 058 146, the contents of which are incorporated herein by reference. Examples of these compounds include cetirizine, in its dihydrochloride form marketed under the tradename Zyrtec®, the (S) enantiomer thereof, levocetirizine, in its dihydrochloride form marketed under the tradename Xyzal® and efletirizine in its dihydrochloride form.

A serious problem encountered with oral formulations of these active compounds is their taste caused by the bitterness of the active compounds of formula I. This is particularly pronounced in chewable and quickly dissolving preparations.

Several attempts have been made in the prior art to mask the bitterness of active agents in general.

U.S. Pat. No. 5,244,881 for example teaches that inclusion into cyclodextrin can mask the bitter taste of the active agent imipramine or its derivative trimipramine. The inclusion complex is prepared by dissolving imipramine or trimipramine and cyclodextrin in a small amount of water or solvent, carefully mixing the mixture obtained and evaporating the said mixture.

However, masking the taste is not always sufficient to obtain palatable pharmaceutical compositions. Good palatability usually further necessitates addition of polyols to the composition. The term "polyol" as used herein includes xylitol, mannitol, sorbitol, dextrose, sucrose, lactose, maltodextrins, alpha cyclodextrins, beta cyclodextrins, gamma cyclodextrins and polysaccharides, but is not limited thereto. Mannitol has proven to be a particularly suitable substance for the improvement of the palatability of preparations containing active compounds of formula I. Such compositions have, however, an important drawback. Compounds of formula I in the presence of certain polyols, including mannitol, can result in undesired reaction products such as for example those disclosed in EP 0 811 374 A1. This side reaction is increased in presence of water and/or by an increase of temperature. The presence of mannitol and other polyols may thus create a stability problem for compounds of formula I.

Until now, to avoid undesired reaction products, there was no choice but to avoid the presence of these polyols in compositions or to coat active compounds of formula I for example with a cellulose or acrylate polymer prior to formulation.

In the first case, using other excipients like microcrystalline cellulose impairs the taste of the tablets by the fact that microcrystalline cellulose is not entirely soluble in water and therefore can leave a sand-like feeling in the mouth.

In the second case, the thickness of the coating necessary for avoiding interactions between the active compounds of formula I and the polyol(s) impedes rapid liberation of the drug from the pharmaceutical form.

EP 0 811 374 A1 teaches that the entire dosage form must be free of reactive alcohols, including polyols. Therefore, palatability improving polyols may not be used in the entire oral composition according to this disclosure. Example 2 of EP 0 811 374, which is stated to demonstrate a preferred embodiment, clearly shows the absence of palatability improving polyols; the only polyol present in this composition is polyethyleneglycol, a high molecular weight polyol (MW 3350) which has a function different from taste masking.

It is the aim of the present invention to overcome this drawback of stability loss in the presence of polyols in a way which is both palatable and avoids disadvantageous changes in product performance.

The problem to be solved by the invention was therefore to improve the taste and palatability of oral compositions containing active compounds of formula I and palatability improving polyols whilst at the same time avoiding any stability impairment and maintaining optimal release kinetics for the active compound.

Taste masking polyols generally are solid and have a molecular weight of less than 3000.

The inventors have found that stability loss caused by interaction of active compounds of formula I and polyols correlates with decreasing molecular weights of the polyols.

TABLE 1

| Molecular weights of some polyols | |
|---|---|
| Polyols | MW |
| Xylitol | 152.15 |
| Mannitol | 182.17 |
| Sorbitol | 182.17 |
| Dextrose | 198.17 |
| Sucrose | 342.30 |
| Lactose | 342.30 |
| Maltodextrins | from 900.00 |
| Alpha cyclodextrin | 972.00 |
| Beta cyclodextrin | 1135.00 |
| Gamma cyclodextrin | 1297.00 |

TABLE 1-continued

Molecular weights of some polyols

| Polyols | MW |
|---|---|
| Microcrystalline cellulose | 36000 |

Generally, polyols with a low molecular weight, such as xylitol, mannitol, sorbitol, dextrose or sucrose (see Table 1) are reactive or very reactive and cause a large amount of undesired reaction products. On the other hand, polyols with a high molecular weight, such as cyclodextrins (see Table 1) are very little reactive.

Surprisingly, this correlation between the molecular weight and the reactivity is not true for lactose. Lactose has the same molecular weight as sucrose but shows practically no reactivity with the active compounds of formula I.

Very reactive polyols may therefore be defined as those polyols having a molecular weight of less than 300. Reactive polyols are those having a molecular weight between 300 and 950, with the exception of lactose.

It has further been found by the inventors that even reactive and very reactive polyols do not cause untolerable amounts of undesired reaction products with the active compounds of formula I if the molar ratio between these polyols and the active compound does not exceed 10. If the molar ratio between reactive or very reactive polyols and the active compound of formula I is not above 5, the percentage of undesired side products is even further minimised.

Based on these findings, the technical problem has been solved according to the present invention by providing a composition prepared from two formulations which contains in the first formulation the active compound of formula I and reactive or very reactive polyols only up to a critical level and which contains in the second formulation the polyols necessary to achieve a pleasant taste but no drug compound. Thereby, formation of undesired reaction products is largely eliminated and the unpleasant taste is efficiently reduced or masked.

This solution of the problem is very different from the teaching in EP 0 811 374 A1. This document teaches that the dosage form should be substantially free of reactive alcohols at the time the immediate-release cetirizine component is introduced into the dosage form and thereafter, thus reactive polyols do have to be excluded from the entire composition. The alcohols disclosed in EP 0 811 374 A1 perform a function completely different from this invention, namely either as solvents (low molecular weight alcohols such as methanol, ethanol, isopropanol and glycerin) or as high molecular weight compounds (polyethylene glycol) to facilitate release of pseudoephedrine. The low molecular weight alcohols are removed before cetirizine is added to prevent undesired reaction products.

According to the present invention reactive polyols may be present in any amount in the second layer. Indeed, the presence of solid polyols with a molecular weight of less than 3000 in the second formulation according to the invention is needed for palatability improvement which is essential for pharmaceutical compositions which are chewable or quickly dissolving.

EP 0 811 374 A1 is not concerned with taste masking as the dosage form is not intended to be dispersed in the mouth but has to be swallowed in its entirety.

The invention relates thus to an oral pharmaceutical composition containing at least two separate formulations:

a first formulation, which contains an active compound selected from 2-[4-(diphenylmethyl)-1-piperazinyl]-acetic acids and their amides having the general formula I

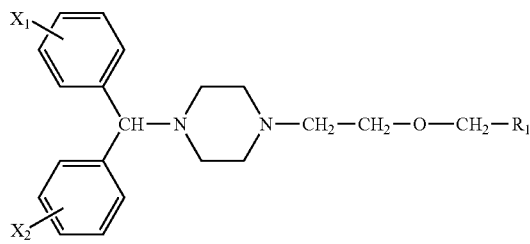

Formula I wherein
$R_1$ is a —COOH group or a —$CONH_2$ group, and
$X_1$ and $X_2$, taken separately, each represent a hydrogen atom, a halogen atom, a straight chain or branched $C_1$-$C_4$ alkoxy group or a trifluoromethyl group, as well as their pharmaceutically acceptable salts, geometrical isomers, enantiomers, diastereomers and mixtures thereof, and which first formulation does not contain polyols having a molecular weight of less than 300 in a molar ratio between the polyol and active compound of formula I above 10; and
a second formulation, which contains one or more solid polyol(s) with a molecular weight of less than 3000 and is free of any drug.

A solid polyol is defined as a polyol which is not liquid at room temperature under atmospheric pressure.

In a preferred embodiment, the first formulation does not contain polyols having a molecular weight of less than 950 in a molar ratio between polyol and active compound of formula I above 10, with the exception of lactose. Since lactose has no significant reactivity with the active compounds of formula I, it may be present in higher ratios.

In another preferred embodiment of the invention, the first formulation does not contain polyols having a molecular weight of less than 300 in a molar ratio between polyol and active compound of formula I above 5.

In a more preferred embodiment, the first formulation does not contain polyols having a molecular weight of less than 950 in a molar ratio between polyol and active compound of formula I above 5 with the exception of lactose.

In a still more preferred embodiment, the first formulation does not contain polyols having a molecular weight of less than 300.

In another still more preferred embodiment, the first formulation does not contain polyols having a molecular weight of less than 950, with the exception of lactose.

The term active compounds of formula I as used in this invention relates to 2-[4-(diphenylmethyl)-1-piperazinyl]-acetic acids and their amides having the general formula I as defined above and also to non-toxic, pharmaceutically acceptable salts, geometrical isomers, enantiomers, diastereomers and mixtures thereof (racemates). In a preferred embodiment, the active compound in the first formulation is cetirizine dihydrochloride, levocetirizine dihydrochloride or efletirizine dihydrochloride.

The term drug includes the active compounds of formula I as well as any other drug.

Preferably, the oral pharmaceutical composition contains only one active ingredient.

Polyols used in the second formulation are typically those which have the ability to reduce the bitter taste of the active compounds of formula I and to improve the palatability of the preparation. Examples include sorbitol, xylitol, maltitol, dextrose, sucrose, polysaccharides and preferably mannitol.

The formulations are prepared in the form of powders, granules, solutions or suspensions.

Solutions or suspensions are used to carry out a coating.

The first and/or second formulation can also contain an alcalinizing agent, preferably sodium citrate. This agent further decreases the production of undesired reaction products between polyols and active compounds of formula I.

The first formulation can contain one or more additional excipients such as colloidal anhydrous silica, microcristalline cellulose, magnesium stearate, flavors or colorants or mixtures thereof.

The first formulation may also contain polyols provided that they do not fall under the provisos of a specific molecular weight in a specific molar ratio as set out above. The first formulation can still further contain non-polyol sweetening agents such as acesulfame K, aspartame, saccharine, saccharine sodium, cyclamate.

Flavors suitable for use in the present invention include essential oils and synthetic flavors such as citrus oils, fruit essences, peppermint oil, spearmint oil, clove oil, oil of wintergreen, anise, eucalyptus and the like. Other artificial flavors known to those skilled in the art are also within the scope of this invention.

All forms of oral composition are envisaged by this invention, including tablets, chewing gums, effervescent tablets or dry syrup.

A dry syrup is defined as a solid formulation such as for example powder or granules destinated to be administered orally in this form or after addition to a liquid.

Accordingly, the present invention relates in a particular embodiment to bi-layer tablets wherein each of the layers is prepared from one of the formulations.

Both formulations of powders are mixed separately and then compressed in a bi-layer rotary tablet press.

The term compression is defined as the reduction in volume of a powder bed due to the application of stress (see "Pharmaceutical powder compaction technology" edited by Göran Alderborn and Chryster Nyström, p. vii, Marcel Dekker, Inc., New York).

In another embodiment, the invention relates to a three-layer tablet wherein an inert layer separates the layers prepared from the two formulations.

Further tablet designs which are also in accordance with this invention include e.g. a "sandwich" design, wherein an inner layer made from one formulation is coated on both sides by layers made from the other formulation or double tablets having an inner core prepared from one formulation and an outer shell made from the other formulation or multi-layer tablets comprising further layers in addition to a first and second layer prepared from the first and second formulation.

A further embodiment of the invention relates to a dry syrup made of a mixture of the two formulations prepared in the form of granules, one containing the active compounds of formula I and one containing the polyol(s).

In this case, the powder formulations are mixed separately and then are compacted, milled and sieved separately and two kinds of granules are obtained. These granules are mixed together to give the final product.

A separate compaction of each formulation is preferred for preparing an effective dry syrup.

The term compaction is defined as the transformation of a powder into a coherent specimen of defined shape by powder compression (see "Pharmaceutical powder compaction technology" edited by Göran Alderborn and Chryster Nyström, p. vii, Marcel Dekker, Inc., New York).

A yet further embodiment of this invention relates to a chewing gum made up for instance of a core made from the first formulation and additionally containing the gum base and a coating made from the second formulation. Alternatively, the chewing gum may be made up of core made from the second formulation and additionally containing the gum base and a coating made from the first formulation.

The gum base used in the present invention for the preparation of a chewing gum may be any suitable gum base known in the art, including natural and synthetic gum bases.

All compositions according to the present invention may contain one or more additional outer coatings.

When a cyclodextrin is present, the molar ratio between cyclodextrin and the active substance of formula I range from 10:1 to 1:1.

The weight ratio between the first formulation and the second formulation is 1:20 to 20:1.

The compositions according to the present invention are dispersible in the mouth and do not necessitate the uptake of water in contrast to the dosage form disclosed in EP 0 811 374A1 which has to be swallowed with water. The compositions of the present invention are for example in the form of orodispersible tablets (tablets to be placed in the mouth where they disperse rapidly before swallowing), they may be chewable or destined to be crunched or sucked.

Experimental results prove that compositions according to the present invention, which are dispersible in the mouth, are bioequivalent to swallowed dosage forms.

Preferably, the compositions according to the present invention are immediate-release formulations, i. e. pharmaceutical formulations having no or little impact on the rate of disposition of the active ingredient to the site of action.

Another embodiment relates to a method of preparing a composition in accordance with the present invention by separately preparing the first formulation, preparing the second formulation and combining the two formulations. The formulations are obtained by usual technologies, such as compression, direct compression, granulation, wet granulation, coating. The technologies are known by the man skilled in the art.

Further taste masking technologies can be used together with this invention. The masking properties may be obtained by applying the masking technologies to one or both formulations.

The present invention is illustrated by the following examples.

EXAMPLE 1

Cetirizine Bi-Layer Chewable Tablets

Two formulations were prepared separately. Tables 2 and 3 give the compositions of these formulations.

TABLE 2

Composition of the cetirizine.2HCl formulation for bi-layer tablets.

| Components | Composition (mg/tablet) |
| --- | --- |
| Cetirizine•2HCl | 10.00 |
| β cyclodextrin | 82.50 |
| Acesulfam K | 3.50 |
| Silica colloidal anhydrous | 1.10 |

TABLE 2-continued

Composition of the cetirizine.2HCl formulation for bi-layer tablets.

| Components | Composition (mg/tablet) |
|---|---|
| Microcrystalline cellulose | 43.86 |
| Flavors | 0.80 |
| Lactose monohydrate | 55.00 |
| Dyes | 0.48 |
| Magnesium stearate | 2.76 |

TABLE 3

Composition of the mannitol formulation for bi-layer tablets.

| Components | Composition (mg/tablet) |
|---|---|
| Mannitol | 241.21 |
| Acesulfam K | 4.69 |
| Flavors | 1.00 |
| Dyes | 0.60 |
| Magnesium stearate | 2.50 |

Cetirizine and mannitol formulations were then compressed on a rotary bi-layer tablet press (eg Courtoy 292/43).

The tablets were placed at 25° C.-60% relative humidity (RH), 30° C.-60% RH and 40° C.-75% RH during 3 months in aluminium/aluminium blisters (Alu/Alu blisters) and high density polyethylene (HDPE) bottles. Table 4 gives the results of this stability study.

TABLE 4

Stability study of cetirizine chewable bi-layer tablets.

| Packaging | Conditions | Cetirizine (%) | Reaction products (%) |
|---|---|---|---|
| HDPE bottles | 25° C. - 60% RH | 100.50 | 0.10 |
|  | 30° C. - 60% RH | 100.00 | 0.20 |
|  | 40° C. - 75% RH | 99.27 | 0.29 |
| Alu/Alu blisters | 25° C. - 60% RH | 96.28 | 0.10 |
|  | 30° C. - 60% RH | 99.32 | BLQ |
|  | 40° C. - 75% RH | 99.99 | 0.22 |

BLQ: below limit of quantification (= 0.1%)

Water content, resistance to crushing, desintegration time, dissolution kinetic were also determined and all the tablets, whatever were the storage conditions, comply with all specifications.

EXAMPLE 2

Cetirizine Dry Syrup

Two formulations were prepared separately. Tables 5 and 6 give the compositions of these formulations.

TABLE 5

Compositions of the cetirizine•2HCl formulations for dry syrups.

| Components | Composition (mg) | | |
|---|---|---|---|
|  | A | B | C |
| Cetirizine•2HCl | 10.00 | 10.00 | 10.00 |
| β cyclodextrin | 82.50 | 82.50 | 82.50 |
| Acesulfam K | 3.00 | 3.00 | 3.00 |
| Microcrystalline cellulose | 279.00 | 83.70 | 0.00 |

TABLE 5-continued

Compositions of the cetirizine•2HCl formulations for dry syrups.

| Components | Composition (mg) | | |
|---|---|---|---|
|  | A | B | C |
| Lactose monohydrate | 0.00 | 195.30 | 0.00 |
| Sodium citrate | 25.50 | 25.50 | 0.00 |
| Total | 400.00 | 400.00 | 95.50 |

TABLE 6

Composition of the mannitol formulation for dry syrups.

| Components | Composition (mg) D |
|---|---|
| Mannitol | 399.60 |
| Flavor | 0.40 |
| Total | 400.00 |

The formulations A, B, C and D were compacted, milled and sieved separately and granules A', B', C' and D' were obtained. The final composition of the dry syrups were obtained by mixing the granules A', B', C' and D' according to the proportions described in table 7.

TABLE 7

Dry syrups compositions.

| Compositions | Components (mg) | | | |
|---|---|---|---|---|
|  | A' | B' | C' | D' |
| E | 400.00 | 0.00 | 0.00 | 400.00 |
| F | 0.00 | 400.00 | 0.00 | 400.00 |
| G | 0.00 | 0.00 | 95.50 | 404.50 |
| H | 100.00 | 0.00 | 0.00 | 200.00 |

The dry syrups were placed at 25° C.-60% RH, 30° C.-60% RH and 40° C.-75% RH during 10 weeks in Aluminium/Aluminium blisters. Table 8 gives the percentages of undesired reaction products detected in the preparations.

TABLE 8

Percentages of undesired reaction products in dry syrups after 10 weeks.

| Compositions | Conditions | Reaction products (%) |
|---|---|---|
| E | 25° C. - 60% RH | 0.00 |
|  | 30° C. - 60% RH | 0.00 |
|  | 40° C. - 75% RH | 0.26 |
| F | 25° C. - 60% RH | 0.00 |
|  | 30° C. - 60% RH | 0.00 |
|  | 40° C. - 75% RH | 0.31 |
| G | 25° C. - 60% RH | 0.00 |
|  | 30° C. - 60% RH | 0.06 |
|  | 40° C. - 75% RH | 0.34 |
| H | 25° C. - 60% RH | 0.03 |
|  | 30° C. - 60% RH | 0.04 |
|  | 40° C. - 75% RH | 0.30 |

All the formulations comply with the specifications.

EXAMPLE 3

Cetirizine Chewing Gum

A composition of a chewing gum made up of a core containing cetirizine, obtained by compression, and a coating containing the polyols is given in table 9.

TABLE 9

Composition of the chewing gum.

| Components | Composition (mg) |
|---|---|
| Core: | |
| Cetirizine•HCl | 10.00 |
| β cyclodextrin | 100.00 |
| Gum base | 660.00 |
| Aspartame | 3.00 |
| Acesulfame K | 2.00 |
| Colloidal silica | 30.00 |
| Talc | 30.00 |
| Magnesium stearate | 20.00 |
| Sweetener | 65.00 |
| Flavors | 80.00 |
| Coating: | |
| Xylitol | 382.50 |
| Mannitol | 85.00 |
| Polyethylene glycol 6000 | 10.00 |
| Titanium dioxide | 10.00 |
| Arabic gum | 10.00 |
| Flavor | 2.50 |
| Carnauba wax | 0.0015 |

As it is the case for bilayer tablets and dry syrups, the chewing gum complies with the stability requirements.

The invention claimed is:

1. A chewable tablet pharmaceutical composition consisting of two layers,
   a first layer comprising a first formulation, which contains an active compound selected from 2-[4-(diphenylmethyl)-1-piperazinyl]-acetic acids and their amides having the general formula I

FORMULA I

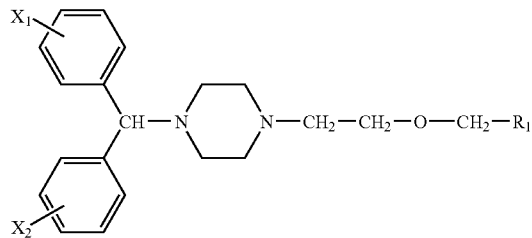

wherein
$R_1$ is a —COOH group or a —CONH$_2$ group, and
$X_1$ and $X_2$, taken separately, each represent a hydrogen atom, a halogen atom, a straight-chain or branched $C_1$-$C_4$ alkoxy group or a trifluoromethyl group as well as their pharmaceutically acceptable salts, geometrical isomers, enantiomers, diastereomers and mixtures thereof, wherein the first layer does not contain polyols having a molecular weight of less than 300 in a molar ratio between the polyol and active compound of formula I above 10; and a second layer comprising a second formulation, which contains one or more solid polyol(s) with a molecular weight of less than 3000, wherein the second layer is free of any drug, wherein the tablet is chewable, and wherein at least one of the formulations further contains an alkalinizing agent.

2. The composition according to claim 1 wherein the first layer does not contain polyols having a molecular weight of less than 950 in a molar ratio between polyol and active compound of formula I above 10, with the exception of lactose.

3. The composition according to claim 1 wherein the first layer does not contain polyols having a molecular weight of less than 300 in a molar ratio between polyol and active compound of formula I above 5.

4. The composition according to claim 1 wherein the first layer does not contain polyols having a molecular weight of less than 300.

5. The composition according to claim 1 wherein the first layer does not contain polyols having a molecular weight of less than 950 in a molar ratio between polyol and active compound of formula I above 5, with the exception of lactose.

6. The composition according to claim 1 wherein the first layer does not contain polyols having a molecular weight of less than 950, with the exception of lactose.

7. The composition according to claim 1 wherein the polyol in the second formulation is mannitol.

8. The composition according to claim 1 wherein the polyol in the second formulation is a polysaccharide.

9. The composition according to claim 1 wherein the alkalinizing agent is sodium citrate.

10. The composition according to claim 1 wherein the first formulation further contains one or more excipients selected from cyclodextrins, colloidal anhydrous silica, microcrystalline cellulose, magnesium stearate, flavors or colorants.

11. The composition according to claim 1 wherein the first formulation further contains non-polyol sweetening agents selected from acesulfame K, aspartame, saccharine, saccharine sodium or cyclamate.

12. The composition according to claim 1 wherein the active compound in the first formulation is cetirizine dihydrochloride, levocetirizine dihydrochloride or efletirizine dihydrochloride.

13. A method of preparing a composition according to claim 1 by separately preparing the first formulation, preparing the second formulation and combining the two formulations.

14. The composition according to claim 1 wherein the first formulation contains cyclodextrine.

15. The composition according to claim 1 wherein the composition does not comprise a coating with cellulose or acrylate.

* * * * *